United States Patent [19]

Mims

[11] 4,082,788

[45] * Apr. 4, 1978

[54] ESTERIFICATION AND EXTRACTION PROCESS

[75] Inventor: Samuel S. Mims, Odessa, Tex.

[73] Assignee: El Paso Products Company, Odessa, Tex.

[ * ] Notice: The portion of the term of this patent subsequent to Nov. 15, 1994, has been disclaimed.

[21] Appl. No.: 851,445

[22] Filed: Aug. 19, 1969

Related U.S. Application Data

[63] Continuation-in-part of Ser. No. 766,476, Oct. 10, 1968.

[51] Int. Cl.$^2$ ............................................. C07C 67/48
[52] U.S. Cl. .............................. 260/465.4; 260/526 R; 260/528; 260/531 R; 260/533 C; 260/535 R; 260/535 P; 260/536; 260/537 R; 260/537 P; 260/537 N; 260/538; 260/540; 260/541; 560/174; 560/179; 560/180; 560/182; 560/189; 560/191; 560/198; 560/204; 560/248; 560/263; 560/265
[58] Field of Search ................ 260/485 S, 485, 533 C, 260/531, 537 D, 465.4; 560/179, 189, 174, 180, 182, 191, 204, 198, 248, 263, 265

[56] References Cited

U.S. PATENT DOCUMENTS

| | | | |
|---|---|---|---|
| 2,824,122 | 2/1958 | Kuceski | 260/537 P |
| 2,968,674 | 1/1961 | Franke et al. | 260/485 R |
| 3,329,712 | 7/1967 | Danly et al. | 260/533 C |

FOREIGN PATENT DOCUMENTS

| | | |
|---|---|---|
| 705,578 | 3/1941 | Germany. |
| 933,714 | 8/1963 | United Kingdom. |

*Primary Examiner*—Jane S. Myers
*Attorney, Agent, or Firm*—Depaoli & O'Brien

[57] ABSTRACT

Organic acids contained in aqueous solution are separated and/or recovered by a process comprising adding an alcohol to the aqueous solution to esterify the acids present, while preferably simultaneously contacting the alcoholic mixture with a water-immiscible solvent and separating layers into an aqueous phase and an organic phase, whereby extraction with the water-immiscible solvent shifts the equilibrium toward the formation of more esters. The esters of the acids may than be recovered as by distillation.

7 Claims, No Drawings

ESTERIFICATION AND EXTRACTION PROCESS

CROSS-REFERENCES TO RELATED APPLICATIONS

This application is a continuation-in-part of my copending application Ser. No. 766,476, filed Oct. 10, 1968.

BACKGROUND OF THE INVENTION

1. Field of the Invention

This invention relates to a process for the recovery and/or isolation of organic carboxylic acids contained in aqueous solutions and more particularly to a process for their separation and/or isolation from each other or other materials as ester derivatives.

2. Description of the Prior Art

The art is well aware of processes for producing useful acids, such as adipic acid, by oxidizing napthenes, cycloaliphatic ketones or cycloaliphatic alcohols with nitric acid in the presence of metal compound oxidation catalysts. Such processes in general involve heating specific materials such as cyclohexane, cyclohexanol and/or cyclohexanone in nitric acid at about 40° to 140° C., generally utilizing nitric acid of about 20 to 90 percent strength, to produce a resulting oxidation mixture comprising the adipic acid together with small amounts of other dicarboxylic acids in admixture with the unused nitric acid and catalyst components. Generally, the art subsequently recovers a substantial amount of the desirable adipic acid by cooling the solution and filtering off the crystallized adipic acid. Such processes for producing the adipic acid are known, for example, in the prior art from U.S. Pat. Nos. 2,791,566; 2,840,607; 3,338,959; 2,971,010; 2,439,513; and 2,557,281.

Adipic acid, of course, is an important intermediate for the production of nylon by subsequent copolymerization with hexamethylenediamine to produce a polyamide capable of being spun into a fiber having a number of desirable characteristics. Many other uses for this material are known to the art.

While the art is well aware of how to recover the major amount of adipic acid, very little attention has been given to procedures for recovery of the remainder of the adipic acid as well as the other dicarboxylic acids contained in the resulting oxidate. My copending application Ser. No. 766,476 mentioned above provides a procedure for recovery of these additional acids as well as the other by-products contained in the mixture.

In the process for nitric acid oxidation of cyclohexanol and/or cyclohexanone, significant amounts of succinic acid and glutaric acid are formed as byproducts in admixture with the adipic acid. Various well known schemes of crystallization have been used heretofore in industry to attempt separation thereof and usually a substantial amount of the adipic acid can be removed by these procedures. Ultimately, however, a mother liquor is obtained from these operations which contains succinic acid, glutaric acid, and a small amount of adipic acid in such proportions that further concentration and crystallization steps will yield only mixtures of these dibasic acids. In addition, as a result of the removal of the adipic acid by crystallization and removal of the water and nitric acid by volatilization, the concentration of the metal catalyst in this final mother liquor becomes relatively high. Hence, loss of these materials, particularly the catalytic components, provides a distinct economic disadvantage as the relatively high proportion of valuable and reusable products is lost.

In my application above-identified, a novel procedure is provided by which the oxidate mixture may be treated with a water-miscible alcohol to esterify the acids present and the resulting esterified products may then be effectively extracted with a water-immiscible solvent such as benzene. The extracted esters may then be obtained as a mixture by removal of the solvent and distilled to separate the esters from each other. After separation, the esters may be easily hydrolyzed back to the individual acids.

In addition to this specific difficultly recoverable dibasic acid mixture however, there are known in the art various other aqueous mixtures of acids, which, because of their similar physical properties, are difficult to recover and isolate by methods known to the art. This is a particularly difficult problem when the acids are contained in dilute aqueous solutions. Such acid mixtures thus include the acid mixtures obtained in the byproduct stream in the air oxidation of cyclohexane to form cyclohexanol and cyclohexanone; the above-mentioned nitric acid oxidation of the cyclohexanol and cyclohexanone; the oxidation of fats and fatty acids which results in a complex mixture of acids with no acid being dominant (as described for example in U.S. Pat. No. 2,662,908); the oxidation of parafinnic hydrocarbons such as refined wax, semi-refined wax, petrolatum, lubricating oil, slack wax, scale wax, foots-oil, etc., in a two-stage process first using air, then nitric acid, which process produces mixtures of dibasic acids, and the like.

Heretofore it has been generally accepted that complex mixtures of this type could not be separated in a sufficiently economical manner to justify the expense involved. Accordingly, such acid mixtures have been used previously in their mixed form or treated as waste.

In addition, aqueous solutions are encountered where one acid will predominate but its physical and chemical characteristics make its isolation and purification difficult (e.g. lactic acid, levulinic acid, etc.). Moreover, it is often desirable to separate acids from water soluble impurities.

It has now been found, as will be described hereinafter, that the principle of the esterification/extraction technique disclosed in my above-identified copending application is applicable to the separation and isolation of many other classes of acids and mixtures thereof and this discovery forms the basis of this invention.

SUMMARY OF THE INVENTION

It is accordingly, one object of the present invention to provide a process for the recovery and/or removal of organic acids contained in aqueous solutions.

A further object of the invention is to provide a method for the recovery of such materials in reusable form uncontaminated by the presence of the other materials.

A still further object is to provide a process by which organic acids may be recovered and easily separated as their esters.

Other objects and advantages of the present invention will become apparent as the description thereof proceeds.

In satisfaction of the foregoing objects and advantages, the process of the present invention provides a procedure for the separation and/or recovery of organic carboxylic acids contained in an aqueous solution which comprises adding a substantially water-miscible alcohol to the aqueous solution to effect esterification of one organic carboxylic acid present, contacting the resultant alcoholic mixture with a water-immiscible solvent, preferably simultaneously with the esterification, and separating the resulting layers into an aqueous phase and an organic phase. The organic phase may then be processed as by distillation to separate the esters which esters may then be hydrolyzed back to the acids if desired.

DESCRIPTION OF PREFERRED EMBODIMENTS

As pointed out above, the process of this invention provides a procedure for the separation and recovery of organic acids contained in admixture with each other in solution, preferably in aqueous solution. According to this invention, it has been discovered that the esterification/extraction concept, applied to a specific acid mixture in my copending application, is generally applicable to a wide variety of acid mixtures contained in aqueous solution and therefore the process has wide application in the art.

Briefly, the process of this invention entails the addition of a substantially water-miscible alcohol to one or a mixture of organic carboxylic acids contained in the aqueous solution. The solution is contacted with a suitable substantially water-immiscible solvent, preferably simultaneously with the esterification step, so that a combination reaction and extraction takes place and, surprisingly, nearly complete removal of the esterified acid(s) from the aqueous phase into the non-aqueous phase is easily effected. The acids are in the form of their ester derivatives in the non-aqueous, or organic, phase. This non-aqueous phase can then be distilled or otherwise processed to recover the solvent and the remaining ester or mixture thereof processed further by one or more of several suitable techniques such as fractional distillation, transestesterification, crystallization or hydrolysis to yield useful products. The aqueous phase may be processed as desired but is preferably distilled to recover the excess alcohol and the water.

As an explanation of the manner in which the process of the invention operates it should be understood that in general, the esterification of organic acids with alcohols is an equilibrium-limited process which may be illustrated by the following equation:

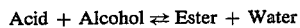

Acid + Alcohol ⇌ Ester + Water

Therefore, because of the equilibrium, in order to achieve high conversions of acids to esters, an important objective in industrial processes, some means of displacing the equilibrium must be used. Several methods are well-known and are enumerated, for example in the Kirk-Othrmer *Encyclopedia of Chemical Technology*, 2nd Edition, V. 8, pp 313–356; "Esterification", by E. E. Leyes; or in *Fatty Acids*, 2nd Edition, Part 2 Section IX, pp 757–984; "Esters and Esterification" by K. S. Markley.

Briefly, these methods of increasing reaction efficiency generally entail such steps as the use of a large excess of alcohol to increase the conversion of acid to ester; the distillation of either the ester or the water out of the reacting mixture; and the removal of water from the reaction by use of dessicants or by chemical means. The method chosen for achieving the increase in conversion depends on the physical and chemical properties of the particular acid, alcohol and ester involved, and of course, on the economics of these various possibilities.

The preparation of esters in the presence of large amounts of water is generally not attempted. Reference to the previous equation shows that the large excess of water tends to shift the equilibrium to the alcohol + acid side. U.S. Pat. No. 2,824,122 for example, discloses a process for preparation of esters from acids in aqueous solutions by use of a water-immiscible alcohol and by distillation of large amounts of water from the reaction medium.

However, using the process disclosed herein it has surprisingly been found that many acids in dilute aqueous solutions containing an acidic catalyst can be efficiently converted to esters using a substantially water-miscible alcohol and a substantially water-immiscible extractive solvent, and that during the esterification process, no distillation or removal of water is required. The process operates by extracting the ester from the aqueous phase into the immiscible solvent phase thereby shifting the equilibrium toward the formation of more ester. In the preferred embodiment of this disclosure these processes, esterification and extraction, occur simultaneously and continuously thereby resulting in an efficient transformation of the acid in aqueous solution into ester in nonaqueous solution.

Generally, the process can be used to particular advantage in situations where, during the simultaneous esterification-extraction process, the acid and alcohol remain almost completely in the aqueous phase while the ester partitions into the non-aqueous phase. For example, this type of relationship has been found to occur in the dibasic acid series using benzene as the extractive solvent and methanol as the miscible alcohol.

On the other hand, using this system of benzene and methanol, the process has been found not to be particularly effective on aqueous mixtures containing the saturated fatty acids because these are extracted into the benzene in the acid form. Thus, the extract in this situation would contain a mixture of esters and free acids. However, the process does work well on the lower saturated fatty acids using a solvent of lower polarity, such as hexane, which does not extract the fatty acids and alcohols but does extract the methyl esters. Likewise the system, benzene-methanol, has been found not to work well with certain poly-functional acids such as malic acid because in these cases the ester does not partition effectively into the benzene and both the acid and ester remain in the aqueous phase (choice of another alcohol such as ethyl alcohol, or extractant such as chloroform, will permit extraction of the diester of malic acid however). Still other acids have such low water solubility that aqueous solutions containing them are not encountered. However for acids with appreciable water solubility that convert to extractable esters, the process disclosed herein has many advantages. For example, water soluble acids can be separated from water soluble impurities by this process. Mixtures of water soluble acids of low volatility can be converted to mixtures of esters of higher volatility which are separable by fractional distillation. Aqueous process streams containing valuable components, such as catalysts, contaminated by organic acids, can be purged of their acids by this process. This esterification process is particularly adaptable to continuous processing and, due to the low temperatures involved, can be used with heat sensitive compounds. The process also finds use in pollution control in treating aqueous waste streams. Moreover, valuable acids difficult to recover by other methods may be recovered using this technique. In addition, esters difficult to prepare by conventional methods may be made by this technique.

The process, because of its wide applicability, may be used to advantage in varied situations. Thus the process may be used to separate organic carboxylic acids from each other where one is left in the aqueous phase either in the form of the acid or ester and the other transferred as the ester to the organic solvent phase. Further the process is applicable to the removal of mixtures of acids from an aqueous phase as an ester mixture; the esters, being more volatile than the acids, may then be fractionated to pure compounds by ordinary distillation. Obviously however, the process is also of importance in various other areas such as to partition or separate poly from mono- or dibasic acids.

The process is useful in these and related areas because of the options which are open to the user through proper choice of the esterifying alcohol and extraction solvent. Thus with any given aqueous solution containing one or more acids, after selecting acid or acids to be removed, one should determine aqueous solubility of the acid or acids, the solubility of the desired or related esters in water and the partitioning characteristics of the esters between the aqueous phase and the extraction solvent. Data of this type is of course generally available in reference works. By this procedure therefore, optimum results can be achieved particularly regarding the amount of acid which can be recovered in the form of its ester, by judicious selection of the esterifying alcohol and extraction solvent.

As suggested above, one of the most interesting and important aspects of the invention is that simultaneous extraction of the aqueous solution as the esters are being formed with the water-immiscible solvent, serves to remove the esters almost on formation. This then upsets the equilibrium of the reaction driving it toward the formation of more esters so that substantially complete esterification and extraction can be achieved by overcoming the equilibrium problem.

As indicated above, the process is applicable to many different types of aqueous solutions of organic acids and particularly those mixtures contained in dilute aqueous solutions. Thus the process is applicable to aqueous solutions of monocarboxylic acids, dicarboxylic, tricarboxylic acids, as well as various polycarboxylic acids. In general however, it can be stated that the process is applicable to any acid or mixture of acids which have appreciable water solubility and which convert to extractable esters.

In general the process is considered applicable to monocarboxylic acids of the formula R—COOH wherein R is an alkyl group, including those which may contain unsaturation or be further substituted, such as acetic acid, propionic acid, butyric acid, pentanoic acid, caproic acid or other fatty acids, lactic acid, levulinic acid, pyruvic acid, glycolic acid, and other substituted acids, etc., and mixtures thereof; dicarboxylic acids of the formula:

wherein R is a single bond or a divalent alkylene bridging group which may contain unsaturation and may be further substituted, such as for example, oxalic acid, malonic acid, succinic acid, glutaric acid, adipic acid, pimelic acid, azelaic acid, itaconic acid, fumaric acid, sebacic acid, malic acid, maleic acid, tartaric acid, tartronic acid, etc., and mixtures thereof. In addition polycarboxylic acids may also be utilized such as tricarballylic acid, citric acid, aconitic acid and the like as well as mixtures thereof. Mixtures of the mono- di- and polycarboxylic acids may also be treated according to the process of the invention.

As indicated above, special advantages of the process of the invention are gained in separation of mixtures of acids which are obtained in industrial processes such as in the production of adipic acid by the nitric acid oxidation of cyclohexanol and cyclohexanone in which a mixture of dibasic acids are formed; the air oxidation of cyclohexane in which a byproduct mixture of dibasic acids are formed; the oxidation of fats and fatty acids with nitric acid to form mixtures of dibasic acids; the oxidation of paraffins of various types; the hydration of maleic acid to produce mixtures of dibasic acids; fermentation processes which yield acids such as lactic acid, oxalic acid, or citric acids; carbohydrate degradation processes which yield levulinic acid, as well as any other method by which mixtures of organic carboxylic acids may be prepared. Therefore, the process is considered to be applicable to any mixture of acids of these types.

As indicated the process is clearly applicable to many situations involving the separation and/or isolation of varied classes of organic carboxylic acids. It can however also be employed for the purification of valuable acids which heretofore have been difficult to obtain in purified form. Exemplary of this class are lactic acid and levulinic acid, which are commercially valuable, as well as related acids of this type.

Lactic acid (2-hydroxypropionic acid) is a commercial chemical consumed at an annual rate of seven to ten million pounds. Unitl December 1963, the acid was made entirely by the fermentation of carbohydrates obtained from molasses, starch hydrolyzates, and milk whey. Currently lactic acid is also made from a by-product stream in acrylonitrile manufacture (Monsanto). Both processes are described, for example, on Kirk-Othmer *Encyclopedia of Chemical Technology*, 2nd Edition "Lactic Acid", V, 12, pp 170–188.

Lactic acid is used as a food acidulant, as an ingredient in emulsifiers for bakery products, in leather tanning, textile finishing, as an ingredient in plasticizers, pharmaceuticals, plastics, solvents, and as a chemical intermediate. The relatively high cost of the acid, however, limits the extent to which it is used. Prices vary from $0.28/lb. for technical grade lactic as a 50% aqueous solution to %0.38/lb for food grade lactic grade as an 88% aqueous solution (cents/lb of 100% lactic acid).

The high cost of lactic acid is in contrast to the low cost of the abundant raw materials from which it can be made. This contrast is due to the difficulties encountered in isolation and purification of the acid from dilute aqueous solutions. Lactic acid is extremely difficult to distill or to crystallize; in addition its extraction from aqueous solution is inefficient. The difficulties in purification of lactic acid have been reviewed for example, in the publication of "Purification of Lactic Acid", E, M, Filachione and C. H Fisher, *Ind. Eng. Chem*, 38, pages 228–232 (1946).

In the present disclosure an improved method for the recovery and purification of lactic acid is described.

Briefly, this process entails the simultaneous esterification and extraction of the ester of lactic acid as one embodiment of the general process described herein.

Solutions of this nature are encountered in the manufacture of lactic acid both by fermentation and by chemical conversion. In addition, lactic acid is present in aqueous waste streams such as for example those encountered in paper manufacture as described for example in U.S. Pat. Nos. 2,750,412 and 2,750,413.

In this invention, there is provided a process for the conversion of lactic acid to an ester of a low molecular weight alcohol. These esters have chemical and physical properties conducive to easy recovery, purification, handling, storage, and further processing. In more detail the process of this disclosure encompasses the following features.

An acidified aqueous solution containing lactic acid, obtained from any of the several possible sources outlined previously, is mixed with a water miscible alcohol. The resulting solution is then extracted under mild heating with an immiscible organic solvent. As a result of these operations, lactic acid in the aqueous phase is transformed into the ester of lactic acid in the organic phase. The organic phase is distilled to recover the immiscible solvent. The residue from this process is then distilled to yield the ester of lactic acid in pure form.

As indicated hereinabove, levulinic acid may also be obtained and purified using the process of this invention. Levulinic acid is a major product of the acid catalyzed degradation of hexose sugars or any cabohydrate yielding them on hydrolysis. The supply of hexoses from cellulose-containing plant materials is, of course, immense and replenishable. Levulinic acid is a reactive organic chemical containing keto and carboxyl groups, as shown by the following structure.

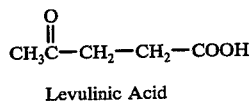

Levulinic Acid

The process of the invention provides a much improved method for the recovery and purification of levulinic acid. Briefly this process entails the simultaneous esterification and extraction of the ester of levulinic acid according to the method of the invention which achieves the efficient removal of levulinic acid from dilute aqueous reaction mixtures in which it is formed. Thus in this invention, there is provided means which results in the conversion of levulinic acid to an ester of a low molecular weight alcohol, which esters have chemical and physical properties conducive to easy recovery, purification, handling and storage.

In this procedure, a carbohydrate-containing material which can yield hexoses on hydrolysis is heated with a small amount of dilute mineral acid, preferably under pressure at an elevated temperature. This basic process is described for example in "Studies on Levulinic Acid. Its Preparation from Carbohydrates by Digestion With Hydrochloric Acid Under Pressure" by R. W. Thomas and H. A. Schuette, JACS 53, 2324-8 (1931). Many modifications and improvements to this basic process are known.

The product of the above reaction will consist of an acidified aqueous solution of levulinic acid mixed with other components such as formic acid, furfural, and including solid "Humus" material. this product is filtered to remove the solids. Then the process disclosed herein is utilized and an alcohol, preferably methanol, is then added to the filtrate. The resultant mixture is then extracted under mild heating with an immiscible organic solvent, preferably benzene. As a result of these operations, levulinic acid in the aqueous phase is transformed into the ester of levulinic acid in the organic phase.

The extract from the above extraction is then preferably distilled at atmospheric pressure to recover the immiscible solvent. The residue from this operation is distilled, preferably under vacuum, to yield the ester of levulinic acid.

The principle on which the above organic acid separations, isolations and purifications is based involves the concept that the esterification/extraction operation, which is preferably conducted simultaneously, provides a reacting solution in which the acid(s) and/or ester(s), are relatively favorably partitionable to the aqueous phase and solvent (organic) phase, respectively. Hence, the alcohol and extractant solvent should be selected, as discussed above, so that the dominant amount of acid will remain in the acid phase and the ester will be partitioned into the organic phase.

As described above, the mixture of acids is treated with an alcohol, preferably by use of a water-miscible alcohol in about equal volume and most preferably in excess, or at least in sufficient amount to esterify all the acids contained therein. By "water miscible alcohol" is meant an alcohol which is substantially soluble in or miscible with water. The alcohols employed are preferably the lower alkyl alcohols, including methanol, ethanol, n-propyl alcohol, isopropyl alcohol, n-butyl alcohol, sec.-butyl alcohol, and the like. In general alcohols containing about 1 to 5 carbon atoms, preferably primary alcohols, are employed to advantage in the present process. In some instances, glycols, such as ethylene glycol or diethylene glycol or ether derivatives thereof may be used to advantage. Methanol represents an especially preferred alcohol for use in this process, however, because of its low cost, high reactivity, and the greater ease of fractionation of its esters. Under other conditions, a less polar alcohol such as ethanol is needed, and particularly with more exotic acid mixtures other alcohols may of course be employed. The alcohol may be added at room temperature or any temperature ranging from about 25° C. up to about the boiling point of the alcohol employed in the process. In general, as the alcohol reacts with the acids contained in the solution to form the alkyl esters thereof, the higher the temperature employed, the faster will be the reaction so that it is generally preferred to conduct this reaction at a slightly elevated temperature in order to obtain maximum esterification in the shortest time possible. A preferred temperature range is about 55° C. up to the boiling point of the alcohol employed, as at room temperature for example, several hours are often required to reach these maximum values whereas under conditions of heat this time is reduced to a few minutes.

In conducting the process, it is highly preferable that a small amount of a catalyst such as an acidic or metallic catalyst be present during the esterification reaction to enable the reaction to reach equilibrium as soon as possible. Generally about 2% to 15% by weight of the total amount of the solution is sufficient. In many instances, the mixture of acids to be treated will be found to contain sufficient acidic catalyst as spent acid to provide the required amount of acid. The mixture resulting from the nitric acid oxidation of cyclohexanol and cyclohexanone, discussed above, containing spent nitric acid, is sufficient in this regard. Acid catalysts which may be employed in this regard include inorganic acids such as sulfuric acid, hydrochloric acid and nitric acid as well as mixtures thereof. Organic acids such as para-toluene sulfonic acid may also be used. Moreover, ion exchange resins in the acid form may also be employed. Hence any type of acid catalyst known in the art to catalyze esterification reactions may be employed. In specialized instances, such as with solutions of amino acids, non-acidic catalysts such as salts of copper or other metals may be used.

After addition of the alcohol to the solution and formation of the esters, to the point of equilibrium, a substantially equal volume of a water-immiscible solvent is added to the mixture and it is allowed to stand at about ambient temperature for sufficient time to obtain separation of layers. Immiscible solvents which have been found to be particularly suitable for this aspect of the process, include the aromatic hydrocarbons, such as benzene, toluene, xylene, ethyl benzene, halogenated aliphatic and aromatic hydrocarbons such as chloroform, chlorobenzene, dichlorbenzene, etc. Aliphatic hydrocarbons such as n-hexane and n-heptane are also suitable. Also, in certain instances, water-immiscible materials such as cycloaliphatic hydrocarbons (e.g. cyclohexane) and pelargonic acid and the like may also be used. In general, any material which is substantially water-immiscible and which will extract a good portion of the esters but will not extract appreciable quantities of the acid or alcohol may be employed in this aspect of the process. Of these several extractants, benzene is an especially suitable immiscible solvent as it is readily available, chemically inert, easily recovered and provides good and consistent results. In some instances however, a more polar solvent is needed and chloroform has been found to be especially suitable. Solvent mixtures may be used.

After the addition of the water immiscible solvent, the two layers are allowed to layer out and the aqueous phase and organic phase separated for further processing.

The aqueous phase and organic phase can be processed in any desirable manner to recover the valuable products contained therein. The aqueous phase contains the excess alcohol, water, any inorganic acid or catalytic components present, as well as a very small amount of the organic acids which were not esterified. This aqueous layer is most suitably processed by subjecting to distillation to remove the alcohol and water fractions. Any inorganic acid or catalytic components will then be in concentrated form in the residue and may be used as desired or discarded. However, any other suitable processing technique may be employed.

The organic phase will be found to contain the water-immiscible solvent and the esters, and may be processed as desired. A very suitable processing technique is to subject the organic phase to distillation by fractionation so as to separate the water-immiscible solvent as one fraction and the one or more esters contained therein as second or separate fractions. This ester mixture is in some cases itself valuable to prepare high molecular weight esters useful as plasticizers. However, the crude esters may be further fractionated to yield in pure form the esters of the individual acids present. These individual ester compounds can then be hydrolyzed either separately or in a mixture to yield the pure acids or can be processed in other ways to yield useful products.

The process has been described above with respect to conducting the process of this invention by the batch method. However, the process can also be conducted in a continuous manner using the combination reaction and extraction procedure. Thus, by use of a series of esterifiers and extraction tanks, a given feed material may be continuously esterified and extracted with the esterifying alcohol and extractant solvent continuously recycled as they are recovered.

Thus in such a continuous procedure, the mixture of acids and the alcohol are mixed in an esterification chamber with any acid necessary to obtain at least partial esterification to the point of equilibrium. Thereafter, this mixture is passed into the extraction chamber where it is admixed with the water-immiscible extractant solvent, the mixing being preferably conducted under countercurrent conditions for good contact. In this chamber, the extractant solvent continuously extracts the esters from the aqueous phase to the organic phase. Further, as this extractive procedure proceeds, the equilibrium of the mixture is upset so that the extraction causes the formation of more esters to the point that all the acids present are converted into their esters and extracted into the organic phase. This esterification/extraction technique therefore is effective to remove the acids in the form of their esters with the esters being transferred to the organic phase.

The resulting mixture is then passed to a separation or settling chamber where the layers are separated as an aqueous phase containing any excess alcohol and water-soluble impurities and an organic phase containing the esters in the extractant solvent.

The aqueous phase is then distilled to remove the excess alcohol and the latter is recycled to the esterification chamber for further reaction with additional acid feed and makeup alcohol. Any acidic catalyst present may also be recovered and recycled to the esterification chamber.

The organic phase is then distilled to remove the extractant solvent and the latter is recycled to the extraction chamber. The resulting residue of substantially pure esters may be treated as described above. Hence, the mixture may be used as such or fractionally distilled to separate the individual esters with subsequent hydrolysis back to the acid if desired. Moreover they may be subjected to transesterification to produce more useful esters such as those of high molecular weight.

The process of this invention thus provides a number of advantages over processes of the art which have been used in an attempt to recover such valuable organic acid components. Hence, in the present process, the removal of any inorganic acids and water from the mixture is not required as, for example, by volatilization, as this is expensive and can be a hazardous step when carried to dryness. Further, distillation of the high boiling acids is not required. Moreover, costly crystallizations and filtration steps are eliminated and the aqueous and organic phases are obtained in uncontaminated form.

The following examples further exemplify certain embodiments of the process but the invention is not to be considered as limited thereto.

In these examples, parts are by weight unless otherwise indicated.

EXAMPLE I

This example illustrates the ineffectiveness of extraction and esterification steps when carried out separately.

An adipic acid mother liquor obtained from a nitric acid oxidation process containing 4% succinic acid, 32% glutaric acid, 5% adipic acid, 16% nitric acid, and 2% catalysts was shaken with an equal volume of benzene periodically during a 24-hour period. The benzene layer was removed and the aqueous layer analyzed. The analysis indicated that the aqueous layer remained essentially unchanged in composition.

A final adipic acid mother liquor, with the composition given above, was mixed with an equal volume of methanol. This yielded a homogeneous solution which was allowed to stand for three weeks. There was no formation of an immiscible layer, and hence the dibasic acids could not be removed.

EXAMPLE II

This example shows the effectiveness of the combination reaction and extraction of the subject process.

A final adipic acid mother liquor, obtained by the nitric acid oxidation of cyclohexanol and cyclohexanone, after crystallization to remove most of the adipic acid, with the composition given in Example I, was mixed with an equal volume of methanol. This solution was then fed continuously to a series of esterifiers, extractors, settlers and feed tanks. For each volume fed of this solution, an equal volume of benzene was fed into the extraction chamber and the system operated in a countercurrent fashion.

The first and second extractors were stirred pots with a twenty-minute hold-up time in each pot. The third extractor was a packed column operated so that the aqueous phase was the continuous phase. Hold-up time of the aqueous phase was about thirty minutes. The aqueous feed tanks were sized so that there was at least an hour's hold-up time in each feed tank. The extractors and feed tanks were maintained at 58° C.

The crude extract recovered from this operation was found on analysis to contain 2.24% dimethyl succinate, 18.59% dimethyl glutarate and 2.46% dimethyl adipate in benzene solution. Distillation of this extract yielded benzene for reuse in the extraction, together with a mixed dimethyl ester fraction.

The crude aqueous phase from the extraction was distilled to remove the excess methanol. After this operation, analysis indicated that the aqueous phase contained 0.29% succinic acid, 0.60% glutaric acid, and 0.01% adipic acid. Concentration of this solution by removal of water under vacuum yielded a solution containing 32.7% nitric acid, 6% catalysts, and about 4% organic acids. This last solution can be reused in the nitric acid oxidation of cyclohexanol/cyclohexanone to adipic acid.

EXAMPLE III

This example shows the effectiveness of various immiscible solvents in the subject process.

A solution containing 8% adipic acid, 20% nitric acid, and 2% catalysts was prepared. One volume of this solution was then mixed with one volume of methanol and one volume of an immiscible solvent. The resulting mixture was then allowed to stand at ambient temperature for 24 hours. The water-immiscible layer was then separated and analyzed for adipate esters. Results are tabulated below.

TABLE I

| Immiscible Solvent | Ester Content of Extract, Wt. % | |
|---|---|---|
| | Dimethyl Adipate | Monomethyl Adipate |
| Benzene | 6.0% | .07% |
| Toluene | 7.0% | Trace |
| Xylene | 6.0% | Trace |
| Ethylbenzene | 6.0% | .05% |
| Chloroform | 7.0% | 0% |
| o-Dichlorobenzene | 5.0% | 0% |
| Pelargonic Acid | 5.0% | 0% |
| Hexane | 1.5% | 0% |
| Cyclohexane | 1.5% | 0% |

This table indicates that solvents characterized by aromaticity, polarizability, and polarity are particularly effective in this process whereas the hexane and cyclohexane do not provide as effective results. The hexane and cyclohexane are effective with other acid mixtures however as shown in Example XII.

EXAMPLE IV

This example shows the effect of time and temperature in the process.

A. Solutions were prepared as in Example III using benzene as the immiscible solvent. The immiscible layer was separated after varying time periods at ambient temperatures and analyzed for adipate esters. Results are tabulated below.

TABLE II

| Time in Contact | Ester Content of Extract, Wt. % | |
|---|---|---|
| | Dimethyl Adipate | Monomethyl Adipate |
| 1 Minute | .05% | .08% |
| 15 Minutes | .75% | .44% |
| 30 Minutes | .78% | .43% |
| 1 Hour | 1.68% | .45% |
| 2 Hours | 3.20% | .48% |
| 3 Hours | 4.40% | .37% |
| 19 Hours | 4.97% | .12% |

B. Solutions consisting of one volume of the final adipic acid mother liquor, described in Example I, and one volume of methanol were prepared. These were allowed to stand for varying periods of time after which they were shaken with one volume of benzene. The benzene layer was separated at once and analyzed. Results are given in the table below.

TABLE III

| Time before Extraction | Ester Content of Extract, Wt. % | | | | | |
|---|---|---|---|---|---|---|
| | Dimethyl | | | Monomethyl | | |
| | Suc-cinate | Glu-tarate | Adi-pate | Suc-cinate | Glu-tarate | Adi-pate |
| 1 Hour | .6 | 7.5 | 1.4 | .07 | 1.33 | .28 |
| 20 Hours | 1.3 | 10.2 | 2.1 | 0 | .47 | .04 |
| 2 Days | 1.3 | 9.9 | 2.0 | 0 | .88 | .07 |
| 3 Days | 1.2 | 9.8 | 1.9 | 0 | .59 | .11 |
| 6 Days | 1.4 | 11.4 | 2.1 | — | — | — |

C. Extractions were carried out exactly as those above, except that the final adipic acid mother liquor-methanol solutions were heated under reflux (65° C.) for varying periods of time prior to extraction with benzene. The results are tabulated below.

TABLE IV

| Time Heated Before Extraction | Ester Content of Extract, Wt. % | | | | | |
|---|---|---|---|---|---|---|
| | Dimethyl | | | Monomethyl | | |
| | Suc-cinate | Glu-tarate | Adi-pate | Suc-cinate | Glu-tarate | Adi-pate |
| 30 min. | 1.2 | 10.1 | 2.0 | 0 | .27 | .04 |
| 1 Hour | 1.2 | 10.2 | 2.0 | 0 | .24 | .03 |

TABLE IV-continued

| Time Heated Before Extraction | Ester Content of Extract, Wt. % | | | | | |
|---|---|---|---|---|---|---|
| | Dimethyl | | | Monomethyl | | |
| | Succinate | Glutarate | Adipate | Succinate | Glutarate | Adipate |
| 2 Hours | 1.2 | 10.6 | 2.1 | 0 | .29 | .03 |
| 3 Hours | 1.2 | 10.6 | 1.9 | .03 | .31 | .10 |

Examination of data in the above tables shows that a maximum value of the ester content of the extract is reached. At room temperature several hours are required to affect this maximum separation; under mild heating this time is reduced to several minutes.

EXAMPLE V

This example illustrates the use of alcohols other than methanol in the process of this invention.

A solution containing 8% adipic acid, 20% nitric acid, and 2% catalysts was prepared. One volume of this solution was mixed with one volume of the alcohol. After standing 30 hours, one volume of benzene was added. After periodic shaking for 6 hours, the layers were separated. Results of the analysis of the benzene layer are tabulated below.

TABLE VI

| Alcohol Used | Ester Content of Extract, Wt. % | |
|---|---|---|
| | Diester | Monoester |
| Methanol | 7% | 0.1% |
| Ethanol | 4% | 1.4% |
| n-Propyl Alcohol | 3% | .6% |
| i-Propyl Alcohol | 0.5% | 1.0% |
| sec-Butyl Alcohol | 0.5% | 1.3% |
| t-Butyl Alcohol | 0% | 0% |

EXAMPLE VI

A sample of the concentrated water extractable by-products isolated from the reactor effluent of the air oxidation of cyclohexane was obtained from a commercial plant. Analysis of this material is given in Table VII.

TABLE VII

| Cyclohexane Oxidation By-Product | |
|---|---|
| Water | 23.0% |
| Succinic Acid | 0.4% |
| Glutaric Acid | 1.8% |
| Adipic Acid | 11.4% |
| Hydroxyhexanoic Acid | 5.9% |
| Other | 57.5% |

This material was fed to a stirred, water-jacketed prereactor at a rate of 4.44 grams/minute. Nitric acid (57% strength) was also fed into this prereactor at a rate of 8.19 grams/minute. The prereactor held 600 ml. and was maintained at a temperature of 57° C. Overflow from this prereactor entered the reactor which was a vessel of similar size maintained at 98° C. Off-gas from this setup contained oxides of nitrogen recoverable as nitric acid which were vented in this laboratory experiment. Overflow from the reactor was collected at a rate of 9.32 grams/minute. This material analyzed as shown in Table VIII:

TABLE VIII

| Reactor Product | |
|---|---|
| Nitric Acid | 9.7% |
| Adipic Acid | 9.1% |
| Glutaric Acid | 7.6% |
| Succinic Acid | 3.3% |

TABLE VIII-continued

| Reactor Product | |
|---|---|
| Oxalic Acid | 1.2% |

This reactor product was mixed with an equal volume of methanol to yield a homogeneous solution. This solution was then placed in a jacketed feed vessel maintained at 50° C., and from this vessel was pumped into the top of a 25 mm. diameter × 900 mm. long jacketed column packed with 4 mm. glass beads. This column was also maintained at 50° C. Benzene was pumped at the same rate into the bottom of this column which was used as a continuous counter-current extractor. Analyses of the benzene extract and the aqueous raffinate are given in Table IX:

TABLE IX

| Extraction of Dibasic Acids Extract Composition | | |
|---|---|---|
| Dimethyl | Oxalate | 0.1% |
| | Succinate | 1.9% |
| | Glutarate | 4.4% |
| | Adipate | 3.8% |
| Monomethyl | Oxalate | 0.1% |
| | Succinate | 0.6% |
| | Glutarate | 0.9% |
| | Adipate | 1.0% |
| Raffinate Composition | | |
| | Oxalic Acid | 0.4% |
| | Succinic Acid | 0.7% |
| | Glutaric Acid | 1.1% |
| | Adipic Acid | 0.6% |

This extract from this step was then distilled at atmospheric pressure to recover the benzene. The residue from this operation was then distilled under vacuum at 50 mm. of mercury using a twenty-plate Oldershaw distillation column to fractionate the dimethyl esters.

The raffinate from the extraction was distilled at atmospheric pressure to recover the excess methanol. The residue from this operation was then distilled under vacuum to remove water and concentrate the nitric acid for reuse in the oxidation reaction.

EXAMPLE VII

The oxidation of fats and fatty acids with nitric acid to form dibasic acids has been known for more than a hundred years; however, the reaction has been used to a very limited extent primarily because of the non-specificity of the reaction which yields a mixture of organic acids in nitric acid usually with no particular dibasic acid predominating. (For example see U.S. Pat. No. 2,662,908).

The process of this invention operating on such reaction products will separate the dibasic acids from the aqueous nitric acid by converting them to diesters of low molecular weight alcohols. These esters may then be separated by ordinary fractional distillation to yield the ester derivatives of the individual acids.

In this example, oleic acid was fed together with 57% nitric acid to a reaction system. The product was separated into an oil phase and an aqueous phase. The aqueous phase was then treated by the process of this disclosure using methanol as the miscible alcohol and benzene as the immiscible solvent. The resulting extract, after partial removal of the benzene was analyzed by gas chromatography and had the composition shown in Table X. Also shown in Table X is the composition of the product obtained by the similar treatment of the mixed fatty acids obtained from tall oil.

TABLE X

| | Esters from Oxidation of Fatty Acids | |
|---|---|---|
| Percent | From Oleic Acid | From Tall Oil |
| Dimethyl | | |
| Oxalate | 3.9 | 3.8 |
| Succinate | 2.8 | 3.7 |
| Glutarate | 4.3 | 3.9 |
| Adipate | 15.7 | 15.6 |
| Pimelate | 11.7 | 8.4 |
| Suberate | 16.2 | 12.8 |
| Azelate | 5.9 | 4.2 |

This mixture of dimethyl esters was separated by fractional distillation into the individual components.

EXAMPLE VIII

This example illustrates the use of a mixture of an unsaturated organic acid and a cyano-substituted organic acid.

Aqueous solutions containing 10% sulfuric acid, 40% methanol, 30% water, and 20% organic acid by weight were prepared using maleic acid and cyanoacetic acid. These were then pumped continuously into the top of a 25 mm. diameter × 900 mm. long water-jacketed column packed with 4 mm. glass beads. The column was maintained at 50° C. An equal volume of benzene was pumped into the bottom of this column which was used as a continuous countercurrent extractor. Dimethyl maleate and methyl cyanoacetate were recovered in amounts representing over 90% of the starting acids from the respective benzene extracts.

EXAMPLE IX

This example illustrates the use of an ion-exchange resin in carrying out the process.

An aqueous solution containing 20% glutaric acid, 40% methanol and 40% water was pumped into the top of a 10 mm. diameter × 400 mm. long column packed with an ion exchange resin in the acid form (Dowex 50W-X2). Benzene was pumped into the bottom of the column kept at ambient temperature. Dimethyl and monomethyl glutarate was found in the benzene extract.

EXAMPLE X

This example illustrates the effect of acid polarity on the extraction efficiency.

A solution was made up containing, by weight, 25% water, 10% sulfuric acid, 40% methanol, 5% oxalic acid, 5% malonic acid, 5% succinic acid, 5% glutaric acid, and 5% adipic acid. This was extracted using the apparatus and under the same conditions as used in Example VIII above, except that two volumes of benzene per volume of the aqueous solution was fed. Analysis of the extract by gas chromatography yielded the results presented In Table XI.

TABLE XI

| | Extraction of Dibasic Acids |
|---|---|
| Acid | Percent Extracted of Amount Fed |
| Oxalic | 32 |
| Malonic | 54 |
| Succinic | 100 |
| Glutaric | 100 |
| Adipic | 100 |

The highly polar oxalic acid and malonic acid were removed with poor efficiency using the methanol/benznene system. However, use of ethyl alcohol to form less polar esters improved the removal of these acids. Alternatively, use of chloroform, a more polar solvent, also improved the removal of these acids.

EXAMPLE XI

This example illustrates the use of a tribasic carboxylic acid in practicing the process.

Citric acid was added to a 40% aqueous solution of methanol containing 10% sulfuric acid. This mixture was then fed to the top of the heated (50° C.) extractor described in Example VIII. An equal volume of benzene was fed to the bottom of this extractor. The benzene extract on cooling deposited a white crystalline material identified by melting point and by nuclear resonance spectroscopy as trimethyl citrate.

EXAMPLE XII

This example illustrates the use of the process in recovery of a saturated fatty acid.

A solution of 30% n-butyric acid, 30% methanol, 30% water and 10% sulfuric acid was prepared and fed into the top of an extractor. An equal volume of hexane was fed into the bottom of the extractor. The extract was collected and distilled. Hexane was recovered as the first fraction. Methyl butyrate (97% pure), representing about 80% of the butyric acid originally present, was then distilled as the second fraction.

In this instance, use of benzene as the extractive solvent was unsatisfactory since relatively large amounts of butyric acid were present in the extract but n-hexane effectively extracted the ester.

EXAMPLE XIII

This example illustrates the use of the process in recovery of an unsaturated tribasic acid.

A solution of 30% aconitic acid (technical grade), 30% methanol, 30% water, and 10% sulfuric acid was prepared and fed continuously into a heated and stirred vessel together with an equal volume of benzene. The temperature of the vessel was maintained at 55° C. and the vessel provided a hold-up time of about 1 hour. Overflow from the vessel went to a cooled separator, maintained at 23° C., where the aqueous and organic phases separated. The organic phase was then washed with water to remove traces of acid and methanol. The resulting organic phase was found to contain trimethyl aconitate in only about a 1% yield.

The experiment was repeated using chloroform as the extractive solvent. After removal of the chloroform from the extract so obtained, the residue was distilled under vacuum and trimethyl aconitate was obtained as a light yellow oil in about 25% yield. Hence, while benzene was not particularly effective here as the extractive solvent, the more polar chloroform worked well.

EXAMPLE XIV

This example illustrates the use of the process in the treatment of mixed dicarboxylic acids obtained by hydration of maleic anhydride.

An aqueous mixture containing 40% maleic anhydride and 6% sulfuric acid was refluxed under atmospheric pressure for 24 hours. After this treatment an equal volume of ethanol was added to the mixture. The resulting homogeneous solution was then extracted with an equal volume of benzene in the stirred vessel as described in Example XIII.

The extract was distilled at atmospheric pressure to remove benzene. The residue from this operation was then distilled under vacuum and a colorless oil was obtained. This oil analyzed as 22% diethyl fumarate, 25% diethyl maleate, 34% diethyl malate, 17% monoethyl fumarate, and 2% unknown.

EXAMPLE XV

This example illustrates how alcohol and solvent polarity affect process operation.

A solution of 14% adipic acid, 7% sulfuric acid, 28% alcohol, and 51% water was fed to the stirred vessel described in Example XIII together with an equal volume of solvent. Analysis of the extracts obtained yielded the results summarized in the table.

TABLE XII

| Esterification/Extraction of Adipic Acid | | |
|---|---|---|
| Solvent | Alcohol | Ratio of Diester to Monoester in Extract |
| Cyclohexane | Methanol | 42.0 |
| Benzene | Methanol | 7.6 |
| Chloroform | Methanol | 3.5 |
| Benzene | Ethanol | 0.7 |

The data in the table show that the less polar solvents show greater selectivity for extraction of the less polar diester; the less polar alcohol, ethanol, permits extraction of larger quantities of the monoester however. The lower boiling diesters were easily separated from the monoesters by fractional distillation to yield products of high purity.

EXAMPLE XVI

This example illustrates the use of the process to prepare esters difficult to prepare by conventional techniques.

A solution of 20% adipic acid, 10% sulfuric acid, 30% water, and 40% ethylene glycol was fed to the stirred vessel described in Example XIII together with an equal volume of chloroform. After removal of the chloroform from the extract, the residue, on cooling, set up as a slightly colored, low melting wax. This material was identified, by gas chromatography and mass spectroscopy of its trimethyl silyl derivative, as bis (2-hydroxyethyl) adipate. The yield of this material was about 35% based on the adipic acid.

EXAMPLE XVII

This example shows the purification of lactic acid.

Technical grade lactic acid, as a 44% aqueous solution (500 grams) was mixed with ethanol (500 grams) and sulfuric acid (96%, 50 grams). This solution was first filtered to remove a small amount of an unidentified precipitate and then placed in a vessel heated to 50° C.

This heated solution was fed into a continuous counter-current extractor near the top and benzene was fed into the extractor at the bottom. The tubular estractor had an internal diameter of 25 mm. and was packed with 4 mm. glass beads. The distance between the entry lines was 900 mm. The extractor was heated by a water jacket as 50° C. water was flowed continuously into the jacket. The benzene, after entering the extractor, flowed upward as small droplets passing through the continuous aqueous phase which flowed slowly downward.

The aqueous phase left the extractor at the bottom. The interface between the immiscible layers was adjusted to remain at a point just below the top of the extractor. The benzene extract left the extractor from the top. Water was added to the extractor at a point about the interface in order to wash traces of methanol and sulfuric acid from the benzene extract. The portion of the extractor between the interface and point of entry of the lactic acid solution (200 ml.) was thus used as a washing section.

The benzene extract so obtained was distilled at atmospheric pressure to recover the benzene. The residue from this operation was then distilled under vacuum. Water-white ethyl lactate (92.4% pure) was obtained in about 50% yield. Reextraction of the raffinate with this recovered benzene using the same process yielded additional ethyl lactate of similar purity.

EXAMPLE XVIII

The experiment of Example XVII was repeated using methanol instead of ethanol. Only about 5% of the lactic acid was extracted as methyl lactate thus indicating the importance of the choice of alcohol.

EXAMPLE XIX

The experiment of Example XVII was repeated using chloroform instead of benzene as the extracting solvent. About 20% of the lactic acid was extracted as ethyl lactate. The chloroform extracted the ethanol from the aqueous solution. In addition, a large tarry residue was obtained form distillation of the ethyl lactate. Thus this example illustrates the importance of the choice of the extracting solvent.

EXAMPLE XX

The experiment of Example XVII was repeated using chloroform instead of benzene and using methanol instead of ethanol. About 50% of the lactic acid was extracted as methyl lactate. Distillation of the extract yielded water-white methyl lactate (98.8% pure).

Much of the work on the esterification/extraction process was done using a methanol/benzene system. The latter examples however, show that the methyl ester of lactic acid has too great an affinity for the aqueous phase to be extracted to a satisfactory degree with benzene.

Thus Examples XVII to XX shown that while a methanol/benzene system is excellent for many acids and mixtures of acids it does not provide the best results in lactic acid purification and therefore different alcohols and extractant solvents must be selected. Thus these examples show that the methyl ester of lactic acid has too great an affinity for the aqueous phase to be extracted to a satisfactory degree with benzene (Example XVIII). However, the use of chloroform, a more polar solvent, provides considerable improvement (Example XX). Alternatively, formation of the less polar ethyl ester permitted benzene to be used effectively (Example XVII). Further, use of the less polar alcohol, ethanol, and the more polar solvent, chloroform, proved not to be satisfactory since the alcohol was extracted from the aqueous phase which served to lower the yield of ester (Example XIX).

The following examples further illustrate the process of this disclosure as applied to the manufacture and purification of levulinic acid.

EXAMPLE XXI

A solution, by weight, of 40% methanol, 30% water, 10% sulfuric acid, and 20% levulinic acid (technical grade) was prepared and placed in a heated vessel at 50°

C. This heated solution was fed (3.7 grams/min.) into a point near the top of a continuous countercurrent extractor. Benzene was fed into the extractor through a line near the bottom at a rate of 3.3 grams/min. The tubular extractor had an internal diameter of 25 mm. and was packed with 4 mm. glass beads. The distance between the points of introduction was 900 mm. The extractor was heated by a water jacket with 50° C. water being passed continuously through the jacket. The benzene, after entering the extractor, flowed upward as small droplets passing through the continuous aqueous phase which flowed slowly downward.

The aqeuous phase left the extractor at the bottom at a rate of 4.1 grams/min. The interface between the immiscible layers was adjusted to remain at a point near the top of the extractor. The benzene extract left the extractor through a line at the top at a rate of 3.8 grams/min. Water (0.9 grams/min.) was added to the extractor through a line near the top in order to wash traces of methanol and sulfuric acid from the benzene extract. The portion of the extractor between the water inlet and the acid solution inlet (200 mm.) was thus used as a washing section.

The benzene extract leaving the extractor contained 13% methyl levulinate accounting for about 62% of the levulinic acid fed. This extract was collected and the benzene was recovered by distillation at atmospheric pressure. The pot residue from this operation was crude methyl levulinate. This was then distilled under vacuum to yield a colorless oil which analyzed as methyl levulinate of 99.3% purity.

Additional levulinic acid was added to the raffinate leaving the extractor and the resulting solution was recycled to the extractor. During this second pass, methyl levulinate continued to be formed and extracted into the benzene.

EXAMPLE XXII

A solution of 200 grams sucrose, 400 grams methanol, 400 grams water, and 400 grams aqueous hydrochloric acid (38%) was prepared. This solution was extracted at 50° C. with an equal volume of benzene in the extraction apparatus described in Example XXI. The benzene extract contained 0.5% methyl levulinate despite the fact that the usual digestion step has been omitted.

The raffinate from this extraction was recycled and extracted again with a second volume of benzene. This extract also contained 0.5% methyl levulinate. Presumably extraction at a higher temperature (under pressure) would increase the rate of formation of methyl levulinate.

EXAMPLE XXIII

A solution of sucrose (23% by weight) and hydrochloric acid (11%) in water was refluxed 5 hours. The solution turned black and solids formed. This solution was cooled and filtered. The filtrate was then mixed with an equal volume of methanol and extracted with an equal volume of benzene as described in Example XXI. The benzene extract contained 3.8% methyl levulinate.

Benzene was removed by distillation at atmospheric pressure. The pot residue from this distillation was then distilled under a vacuum (50 mm. of Hg) to yield methyl levulinate (99.27% pure) as a colorless oil.

The invention has been described herein with reference to certain preferred embodiments but is not to be considered as limited thereto.

What is claimed is:

1. In a continuous process for the treatment of aqueous solutions which contain mixtures of at least two difficultly separable aliphatic carboxylic acids which have appreciable water solubility and which are convertible to extractable esters, the improved process which comprises:
   (a) continuously contacting said aqueous solution with a water-miscible esterifying liquid selected from the group consisting of lower alkyl alcohols, alkylene glycols, their ether derivatives and mixtures thereof, at a temperature of from 25° C. to the boiling point of the solvent used and in a sufficient amount to esterify at least two of the aliphatic acids present and in the presence of an esterification catalyst to form an esterifying mixture;
   (b) continuously contacting said esterifying mixture countercurrently simultaneously with the esterification reaction, with a substantially water-immiscible organic solvent selected being from the group consisting of aromatic hydrocarbons, aliphatic hydrocarbons, halogenated aliphatic hydrocarbons, halogenated aromatic hydrocarbons, cycloaliphatic hydrocarbons and mixtures thereof, in a sufficient amount to extract the esters formed into said organic solvent substantially as they are formed; said countercurrent contact being carried out by passing said esterifying mixture into at least one extractor and passing said organic solvent into at least one said extractor countercurrent to said esterifying mixture and continuing said contact for a sufficient time to extract the esters formed into said organic solvent; (c) removing the resulting mixture from the said at least one extractor, passing to at least one settler and permitting the mixture to layer out and form an organic phase and an aqueous phase, said organic phase containing esters of the said aliphatic acids dissolved in said water-immiscible organic solvent and said aqueous phase containing water, any excess water-miscible esterifying liquid, any unesterified aliphatic acids and esterification catalysts;
   (d) separating said organic phase and said aqueous phase and passing said organic phase and aqueous phase to separate distillation stages;
   (e) distilling said organic phase to remove the water-immiscible organic solvent and recycling said organic solvent to at least one of said extractors, and recovering the organic esters of the aliphatic acids;
   (f) distilling the aqueous phase to remove any excess water-miscible esterifying liquid and any unesterified aliphatic acids;
   (g) recycling said water-miscible esterifying liquid and unesterified aliphatic acids to the initial esterification step.

2. A process according to claim 1 wherein the aqueous solution contains about 2 to 15 weight percent of an acidic or metallic catalyst.

3. A process according to claim 2 wherein the water-miscible esterifying liquid is a primary straight or branch chain alkyl alcohol having one to about five carbon atoms in the alkyl group.

4. A process according to claim 3 wherein the water-immiscible solvent is selected from the group consisting of benzene, toluene, xylene, ethylbenzene, chloroform, chlorobenzene, dichlorobenzene, n-hexane and n-heptane.

5. A process according to claim 4 wherein the aliphatic acids are selected from the group consisting of mono-carboxylic acids, dicarboxylic acids, polycarboxylic acids, or mixtures thereof, the alcohol is a primary alcohol having 1 to 5 carbon atoms and the water-immiscible organic solvent is an aromatic hydrocarbon.

6. A process according to claim 1 wherein the mixture or organic esters in (e) is fractionally distilled to recover the individual organic esters of each aliphatic acid esterified.

7. A process according to claim 6 wherein the esterifying liquid is methanol, the water-immisicible solvent is benzene, and these materials are employed in a volume equal to the volume of liquid being treated.

* * * * *